United States Patent
Hill (10) Patent No.: US 8,007,717 B2
(45) Date of Patent: Aug. 30, 2011

(54) METHOD AND APPARATUS FOR DECONTAMINATING A REGION WITHOUT DEHUMIDIFICATION

(75) Inventor: Aaron L. Hill, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 903 days.

(21) Appl. No.: 11/838,327

(22) Filed: Aug. 14, 2007

(65) Prior Publication Data

US 2009/0047174 A1   Feb. 19, 2009

(51) Int. Cl.
*A61L 2/20* (2006.01)
(52) U.S. Cl. ............... 422/3; 422/28; 422/37; 422/105; 422/108
(58) Field of Classification Search ............... 422/3, 28, 422/37, 105, 108, 292, 298
See application file for complete search history.

(56) References Cited

U.S. PATENT DOCUMENTS

| | | | |
|---|---|---|---|
| 4,204,037 A | 5/1980 | Dill et al. ........................... 435/3 |
| 4,241,010 A | 12/1980 | Baran ............................... 422/2 |
| 4,591,485 A | 5/1986 | Olsen et al. ..................... 422/20 |
| 4,843,867 A | 7/1989 | Cummings ...................... 73/23 |
| 4,863,688 A | 9/1989 | Schmidt et al. ................. 422/28 |
| 4,908,188 A | 3/1990 | Jefferis et al. ................. 422/111 |
| 4,952,370 A | 8/1990 | Cummings et al. ............. 422/28 |
| 4,956,145 A | 9/1990 | Cummings et al. ............. 422/28 |
| 5,020,481 A | 6/1991 | Nelson .......................... 122/494 |
| 5,114,670 A | 5/1992 | Duffey ............................ 422/24 |
| 5,122,344 A | 6/1992 | Schmoegner ................. 422/111 |
| 5,173,258 A | 12/1992 | Childers ......................... 422/27 |
| 5,418,167 A | 5/1995 | Matner et al. ................. 435/288 |
| 5,492,672 A | 2/1996 | Childers et al. ................ 422/28 |
| 5,508,009 A | 4/1996 | Rickloff et al. .............. 422/292 |
| 5,650,693 A | 7/1997 | Campbell et al. ........ 315/111.21 |
| 5,770,393 A | 6/1998 | Dalmasso et al. ............... 435/31 |
| 5,788,925 A | 8/1998 | Pai et al. ........................... 422/3 |
| 5,866,356 A | 2/1999 | Albert et al. ..................... 435/31 |
| 5,872,359 A | 2/1999 | Stewart et al. ........... 250/339.12 |
| 5,876,664 A | 3/1999 | Childers et al. ................ 422/28 |
| 5,882,590 A | 3/1999 | Stewart et al. ................. 422/28 |
| 5,906,794 A | 5/1999 | Childers ......................... 422/28 |
| 5,993,886 A * | 11/1999 | Polster .......................... 426/614 |

(Continued)

FOREIGN PATENT DOCUMENTS

WO   WO 97/47331   12/1997

(Continued)

OTHER PUBLICATIONS

U.S. Appl. No. 11/421,265, filed May 31, 2006, Buczynski, entitled: Decontamination System With Air Bypass.

(Continued)

*Primary Examiner* — Sean E Conley
(74) *Attorney, Agent, or Firm* — Kusner & Jaffe; Michael A. Centanni (57) ABSTRACT

A method and apparatus for decontaminating a region with a gaseous or vaporous decontaminant (e.g., vaporized hydrogen peroxide) without dehumidification (e.g., without the use of a dryer). The saturation concentration of the decontaminant inside the region is monitored, and the concentration of the decontaminant inside the region is regulated to prevent condensation of the decontaminant. The bioburden reduction is continuously monitored during a decontamination phase to ascertain successful completion of a decontamination process in accordance with a target bioburden reduction.

20 Claims, 8 Drawing Sheets

U.S. PATENT DOCUMENTS

| | | | | |
|---|---|---|---|---|
| 6,156,267 | A | 12/2000 | Pai et al. | 422/3 |
| 6,369,112 | B1 | 4/2002 | Xia | 514/635 |
| 6,379,615 | B1 | 4/2002 | Ogle | 422/28 |
| 6,387,648 | B1 | 5/2002 | Levi et al. | 435/26 |
| 6,428,746 | B1 | 8/2002 | Muscarella et al. | 422/3 |
| 6,455,272 | B1 | 9/2002 | Gillis | 435/31 |
| 6,513,378 | B1 | 2/2003 | Love, Jr. | 73/313 |
| 6,528,016 | B1 | 3/2003 | Kohler et al. | 422/28 |
| 6,718,077 | B1 | 4/2004 | Ferreira et al. | 385/12 |
| 6,787,105 | B2 | 9/2004 | Robbins | 422/22 |
| 6,803,728 | B2 | 10/2004 | Balasubramaniam et al. | 315/149 |
| 6,953,549 | B2 | 10/2005 | Hill et al. | 422/30 |
| 7,157,046 | B2 | 1/2007 | McVey et al. | 422/28 |
| 7,186,374 | B2 | 3/2007 | Zelina et al. | 422/28 |
| 7,238,330 | B2 | 7/2007 | Hill et al. | 422/292 |
| 7,252,800 | B2 | 8/2007 | Jacobs et al. | 422/33 |
| 2002/0114727 | A1 | 8/2002 | McVey et al. | 422/4 |
| 2002/0159915 | A1 | 10/2002 | Zelina et al. | 422/3 |
| 2003/0031589 | A1 | 2/2003 | Martin et al. | 422/28 |
| 2003/0063997 | A1 | 4/2003 | Fryer et al. | 422/3 |
| 2003/0138344 | A1 | 7/2003 | Mielnik et al. | 422/2 |
| 2003/0164091 | A1 | 9/2003 | Hill et al. | 95/90 |
| 2004/0076358 | A1 | 4/2004 | Ferreira et al. | 385/12 |
| 2004/0105758 | A1 | 6/2004 | Ross | 417/44.1 |
| 2004/0154965 | A1 | 8/2004 | Baum et al. | 210/85 |
| 2005/0079096 | A1 | 4/2005 | Brown-Skrobot et al. | 422/24 |
| 2005/0252274 | A1 | 11/2005 | Centanni | 73/23.2 |
| 2005/0274656 | A1 | 12/2005 | McKinney | 210/86 |
| 2005/0276723 | A1 | 12/2005 | Sundaram et al. | 422/28 |
| 2006/0008379 | A1 | 1/2006 | Mielnik et al. | 422/32 |
| 2006/0061953 | A1 | 3/2006 | Le | 361/684 |
| 2006/0088441 | A1 | 4/2006 | Hill | 422/30 |
| 2006/0099106 | A1 | 5/2006 | Watling et al. | 422/3 |
| 2006/0257877 | A1 | 11/2006 | Anderle et al. | 435/6 |
| 2007/0014691 | A1 | 1/2007 | Lin et al. | 422/62 |
| 2007/0098592 | A1 | 5/2007 | Buczynski et al. | 422/3 |
| 2008/0038166 | A1 | 2/2008 | Hill et al. | 422/292 |
| 2008/0267818 | A1 | 10/2008 | Hill et al. | 422/28 |

FOREIGN PATENT DOCUMENTS

| | | |
|---|---|---|
| WO | WO 03/082355 | 10/2003 |

OTHER PUBLICATIONS

U.S. Appl. No. 11/463,608, filed Aug. 10, 2006, Hill, entitled: Modular Decontamination System.

U.S. Appl. No. 11/740,973, filed Apr. 27, 2007, Hill, entitled: Vaporized Hydrogen Peroxide Probe Calibration Rig.

U.S. Appl. No. 11/741,069, filed Apr. 27, 2007, Hill, entitled: Vaporized Hydrogen Peroxide Decontamination System With Concentration Adjustment Mode.

U.S. Appl. No. 11/741,299, filed Apr. 27, 2007, Hill, entitled: Hydrogen Peroxide Vaporizer.

\* cited by examiner

METHOD AND APPARATUS FOR DECONTAMINATING A REGION WITHOUT DEHUMIDIFICATION

FIELD OF THE INVENTION

The present invention relates generally to the art of decontamination using a gaseous or vaporous decontaminant, and more particularly to a method and apparatus for decontaminating a region with a gaseous or vaporous decontaminant under humid conditions.

BACKGROUND OF THE INVENTION

One commonly used decontaminating agent is vaporized hydrogen peroxide. During a decontamination phase of a typical hydrogen peroxide vapor decontamination cycle, an aqueous solution of hydrogen peroxide (e.g., about 30% to 59% hydrogen peroxide, by weight) is injected into a vaporizer. The vaporizer vaporizes the aqueous solution of hydrogen peroxide, thereby generating a hydrogen peroxide vapor that is carried into an enclosure defining a region (such as a room, an isolator, a cabinet or a decontamination chamber) by a carrier gas (e.g., air). As used herein the term "decontamination" refers to the inactivation of bio-contamination, and includes, but is not limited to, sterilization and disinfection. "Decontaminant" refers to a chemical agent that effects decontamination.

Gaseous and vaporous decontamination systems rely on maintaining certain process parameters in order to achieve a target decontamination assurance level. For hydrogen peroxide vapor decontamination systems, those parameters include, but are not limited to, concentration of the hydrogen peroxide vapor, degree of saturation, temperature, pressure, and exposure time. By controlling these parameters, the desired decontamination assurance levels can be successfully obtained while avoiding condensation of the hydrogen peroxide due to vapor saturation. In this regard, condensation of hydrogen peroxide is ordinarily not desired, since it can result in increased aeration time, corrosion, and hazardous conditions. Some studies have also shown that condensation of hydrogen peroxide may also inhibit the effectiveness of the hydrogen peroxide vapor.

Considering only temperature, condensation of hydrogen peroxide occurs when the concentration of hydrogen peroxide vapor exceeds a saturation concentration (also referred to herein as a "dew point" concentration) for a given temperature. In order to avoid condensation of the hydrogen peroxide during a decontamination phase, care must be taken to insure that the actual concentration of hydrogen peroxide in the region does not exceed the saturation concentration for the temperature in the region.

Atmospheres of hydrogen peroxide vapor typically include water vapor. As the decontaminant (i.e., vaporized hydrogen peroxide) is injected into a region, the concentration of water vapor found in the region will increase due to the concentration of water in the aqueous solution of hydrogen peroxide and the degradation of vaporized hydrogen peroxide into water vapor. In addition to showing a temperature dependency, the saturation concentration of hydrogen peroxide is also a function of water vapor concentration. For example, it is observed in a vaporized hydrogen peroxide/water vapor atmosphere that the higher the actual concentration of water vapor, the lower the saturation concentration of hydrogen peroxide.

A decrease in the water vapor concentration within the region will have the beneficial effect of increasing the saturation concentration of the hydrogen peroxide. Therefore, in a typical vaporized hydrogen peroxide decontamination system, a dryer (e.g., a desiccant dryer) is used to remove moisture from the region being decontaminated.

Figure 1:
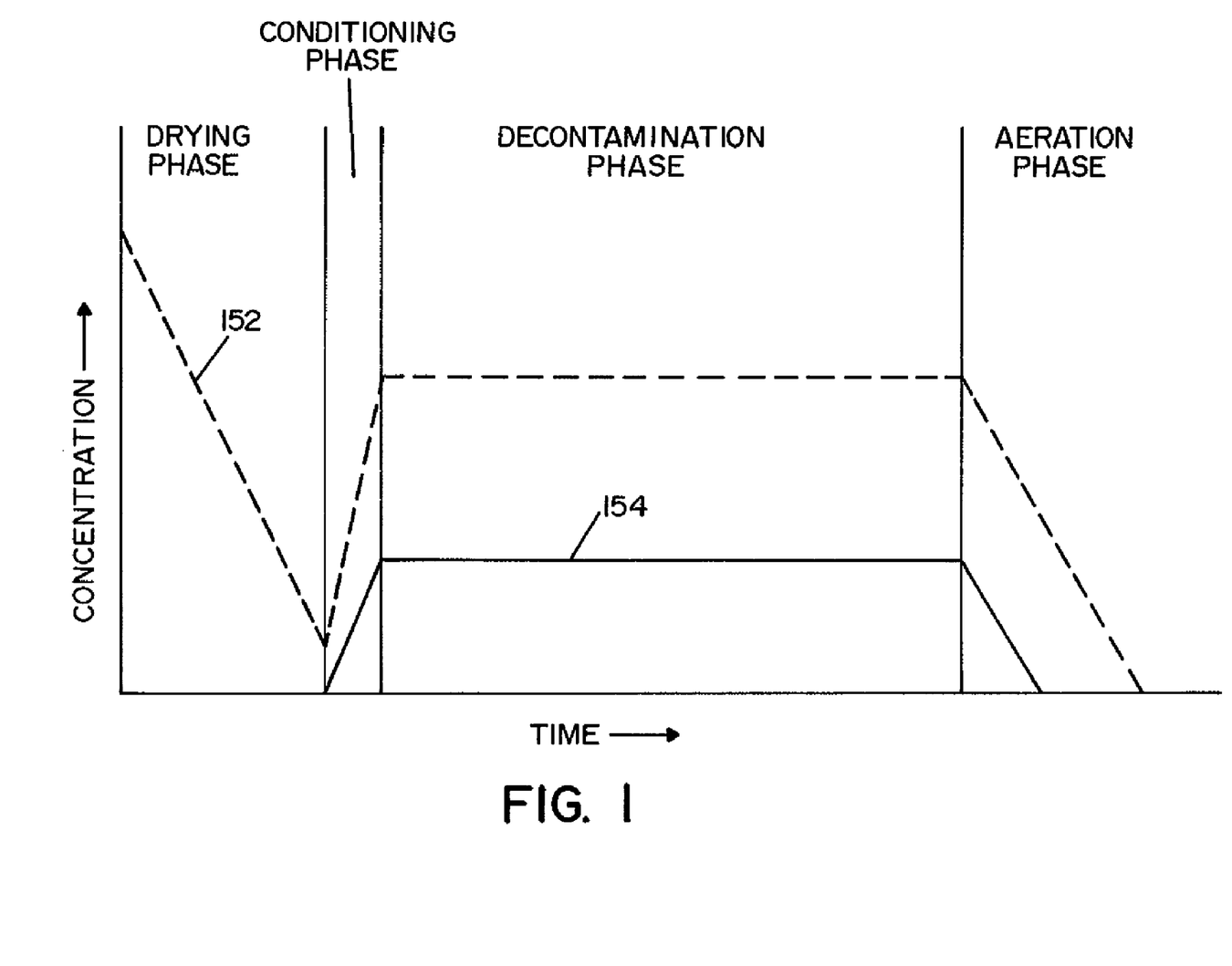
FIG. 1 is a graph depicting the phases of a typical vaporized hydrogen peroxide treatment cycle, with respect to concentration of hydrogen peroxide and water.

FIG. 1 illustrates the phases of a typical vaporized hydrogen peroxide treatment cycle for a vaporized hydrogen peroxide decontaminating system. The cycle includes a drying phase, a conditioning phase, a decontamination phase and an aeration phase. The water vapor concentration and hydrogen peroxide concentration during each phase of the cycle are respectively shown by reference lines 152 and 154. During the drying phase, the region is dried to a low humidity level using a dryer (e.g., a desiccant dryer). A conditioning phase follows the completion of the drying phase. During the conditioning phase, vaporized hydrogen peroxide is injected into the region at a relatively high rate to rapidly increase the hydrogen peroxide concentration within the region. After completion of the conditioning phase, the decontamination phase commences. During the decontamination phase, injection of the vaporized hydrogen peroxide is regulated to maintain a substantially constant hydrogen peroxide concentration within the region for a required exposure time. The dryer is used during the decontamination phase to remove water vapor from the region that is produced from the breakdown of vaporized hydrogen peroxide into water vapor and oxygen. An aeration phase follows the completion of the decontamination phase. During the aeration phase, injection of vaporized hydrogen peroxide into the region is stopped and hydrogen peroxide is removed from the region until the hydrogen peroxide concentration is below an allowable threshold (e.g., 1 ppm).

Recently, there has been a need to decontaminate regions having larger volumes, such as laboratories, offices, hotel rooms, cruise ships, airport terminals, and the like. As discussed above, minimizing water vapor concentration is important to preventing condensation of hydrogen peroxide. In order to remove moisture from such large regions during the drying and decontamination phases, it may be necessary to use a large capacity dryer, multiple dryers, an on-site dryer regenerator, or a combination thereof.

Figure 2:
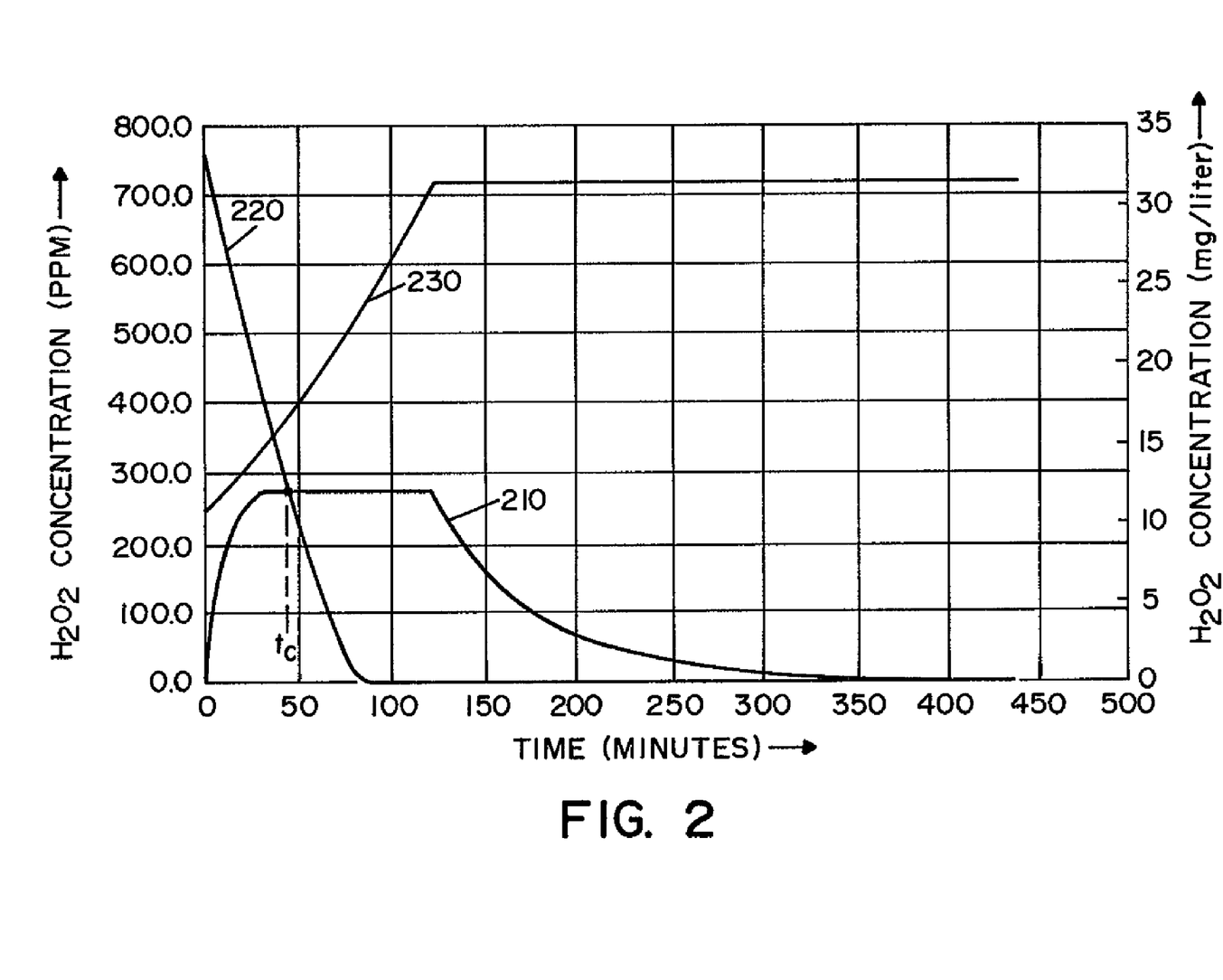
FIG. 2 shows a graph of hydrogen peroxide concentration, water concentration, and $H_2O_2$ dew point concentration as a function time, during the conditioning and decontamination phases of an existing decontamination system, without dehumidification (i.e., no dryer)

With existing decontamination system control strategies, condensation poses a significant problem in the absence of dryers. In this regard, the example shown in FIG. 2 illustrates the change in the $H_2O_2$ dew point concentration (reference line 220) and water concentration (reference line 230), as the hydrogen peroxide concentration (reference line 210) is varied. At time $t_c$, condensation of the hydrogen peroxide occurs, since the hydrogen peroxide concentration equals the $H_2O_2$ dew point concentration. The increasing water concentration continues to reduce the $H_2O_2$ dew point concentration. The parameters for the vaporized hydrogen peroxide decontamination system model associated with the data of FIG. 2 are as follows:

$T_{REGION}$ (temperature in the region)=25° C.
$RH_{INITIAL}$ (initial relative humidity in the region)=40%
$V_{REGION}$ (volume of region)=119 m³
Required $H_2O_2$ Concentration for Decontamination Phase=250 ppm
$t_{EXPOSURE}$ (Required Exposure Time)=90 minutes
Aqueous solution of hydrogen peroxide=35% $H_2O_2$/65% water, by weight It should be understood that the system model does not account for adsorption or catalytic effects, but does account for vaporized hydrogen peroxide "half life."

As can be observed from FIG. 2, if water vapor is not removed from the region by use of a dryer, the water concentration in the region will increase in response to the introduction of more vaporized hydrogen peroxide and water vapor into the region. As a result, it becomes increasingly difficult to prevent condensation of the hydrogen peroxide.

The present invention provides a method and apparatus for decontaminating a region without the need for a dryer, while also preventing condensation of the hydrogen peroxide.

SUMMARY OF THE INVENTION

In accordance with an embodiment of the present invention, there is provided a method for decontaminating a region with a vaporized decontaminant, the method comprising the steps of: (a) supplying vaporized decontaminant into the region for obtaining at least a minimum concentration level of the vaporized decontaminant in the region; (b) monitoring the concentration of the vaporized decontaminant in the region; (c) determining the dew point concentration of the vaporized decontaminant in the region; (d) regulating the supply of vaporized decontaminant into the region to maintain the concentration of vaporized decontaminant to at least a predetermined amount below the dew point concentration of the vaporized decontaminant; (e) calculating a total bioburden reduction within the region for a time period; (f) determining whether a decontamination process is complete by comparing the total bioburden reduction within the region to a target bioburden reduction; and (g) continuing the decontamination process until the total bioburden reduction within the region has achieved the target bioburden reduction.

In accordance with another aspect of the present invention, there is provided a vapor decontamination system for decontaminating a region, said system comprising: a decontaminant supply for providing a supply of liquid decontaminant; a vaporizer for generating a vaporized decontaminant, said vaporizer receiving liquid decontaminant from the decontaminant supply; a circulating system for supplying said vaporized decontaminant to said region; and control means programmed to: (a) monitor the concentration of the vaporized decontaminant in the region; (b) determine the dew point concentration of the vaporized decontaminant in the region; (c) regulate the supply of vaporized decontaminant into the region to maintain the concentration of vaporized decontaminant at least a predetermined amount below the dew point concentration of the vaporized decontaminant; (d) calculate a total bioburden reduction within the region for a time period; and (e) determine whether a decontamination process is complete by comparing the total bioburden reduction within the region to a target bioburden reduction, wherein the decontamination process is continued until the total bioburden reduction within the region has achieved the target bioburden reduction.

In accordance with still another aspect of the present invention, there is provided a method for decontaminating a region with vaporized hydrogen peroxide, the method comprising the steps of: (a) supplying vaporized hydrogen peroxide into the region; (b) monitoring the concentration of the vaporized hydrogen peroxide in the region; (c) regulating the supply of vaporized hydrogen peroxide into the region to maintain the concentration of vaporized hydrogen peroxide below the dew point concentration of the vaporized hydrogen peroxide; (d) repeatedly calculating a total bioburden reduction within the region during a decontamination process, said total bioburden reduction calculated for one or more time periods during the decontamination process; (e) determining whether the decontamination process is complete by comparing the calculated total bioburden reduction to a target bioburden reduction; and (f) continuing the decontamination process until the calculated total bioburden reduction within the region has achieved the target bioburden reduction.

An advantage of the present invention is the provision of a method and apparatus for decontaminating a region without the need for dehumidification.

Another advantage of the present invention is the provision of a method and apparatus for decontaminating a region without the need for a drying apparatus.

Another advantage of the present invention is the provision of a method and apparatus for decontaminating a region, wherein the concentration of a decontaminant varies during a decontamination procedure.

Still another advantage of the present invention is the provision of a method and apparatus for decontaminating a region wherein condensation of hydrogen peroxide is prevented or minimized.

Yet another advantage of the present invention is the provision of a method and apparatus for decontaminating a region wherein the bioburden level is continuously monitored throughout a decontamination procedure.

These and other advantages will become apparent from the following description of an embodiment taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF PREFERRED EMBODIMENT

Figure 3:
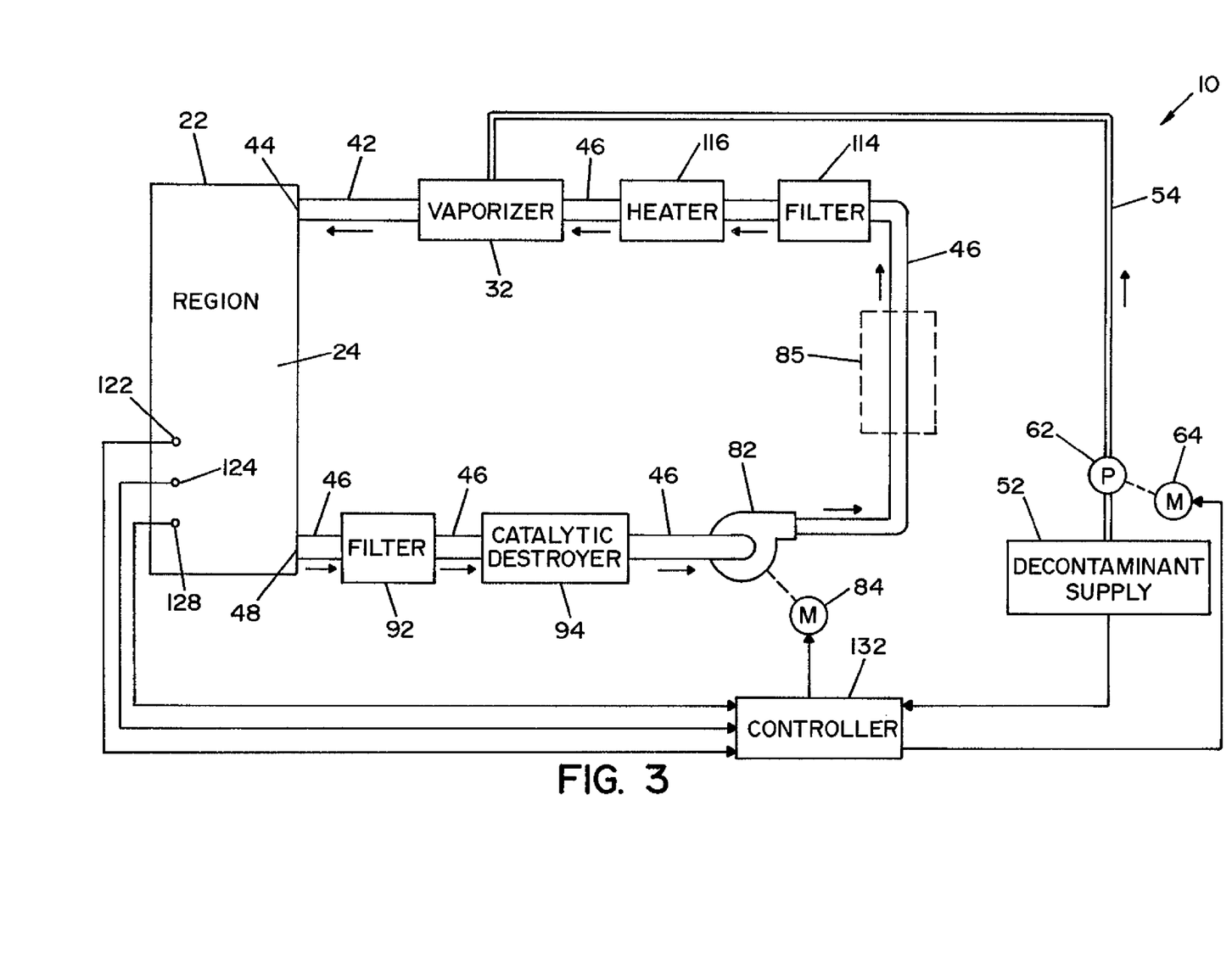
FIG. 3 is a schematic view of a vaporized hydrogen peroxide decontamination system according to an embodiment of the present invention.

Referring now to the drawings wherein the showings are for the purpose of illustrating an embodiment of the invention only, and not for the purpose of limiting same, FIG. 3 shows a vaporized hydrogen peroxide (vhp) decontamination system 10, illustrating an embodiment of the present invention. While a "closed loop" system is illustrated, it is contemplated that the present invention may also be used in connection with an "open loop" or "flow through" system. In the embodiment shown, system 10 includes an enclosure 22 (e.g., room, laboratory, office, cruise ship, airport terminal, isolator, cabinet, decontamination chamber, or the like) that defines a region 24. It is contemplated that various articles may also be disposed within region 24.

A vaporizer 32 is connected to region 24 of enclosure 22 by means of a supply conduit 42. Supply conduit 42 defines a fluid inlet 44 to region 24. Vaporizer 32 is connected to a liquid decontaminant supply 52 by a feed line 54. Decontaminant supply 52 may also include a conventionally known balance device with reservoir (not shown) or pressure transducer with reservoir (not shown) for providing data indicative of the quantity (i.e., mass) of liquid decontaminant being supplied to vaporizer 32. In the illustrated embodiment the liquid decontaminant is an aqueous solution of hydrogen peroxide (e.g., 30% to 59% hydrogen peroxide, by weight).

A pump 62, driven by a motor 64, is provided to convey metered amounts of the liquid decontaminant to vaporizer 32 where the decontaminant is vaporized by conventionally known means. As conventionally known, the amount of liquid decontaminant being metered to vaporizer 32 (i.e., the injection rate) can be determined using the quantity of liquid decontaminant depleted from decontaminant supply 52, as indicated by components such as the balance device or pressure transducer described above. Alternatively, pump 62 is provided with an encoder (not shown) that allows monitoring of the amount of decontaminant being metered to vaporizer 32. If an encoder is provided with pump 62, the balance device or pressure transducer is not required, but may still be used as a secondary measurement device. Motor 64 may have variable speeds to provide variable injection rates.

Enclosure 22 and vaporizer 32 are part of a circulation system that includes a return conduit 46 that connects enclosure 22 (and region 24) to vaporizer 32. Return conduit 46 defines a fluid outlet 48 to region 24. A blower 82, driven by a motor 84, is disposed within return conduit 46 between enclosure 22 and vaporizer 32. Blower 82 is operable to circulate decontaminant and air. A first filter 92 and catalytic destroyer 94 are disposed in return conduit 46 between blower 82 and enclosure 22, as illustrated in FIG. 1. First filter 92 is preferably a "high efficiency particulate air" (HEPA) filter and is provided to remove contaminants flowing through system 10. Catalytic destroyer 94 is operable to destroy hydrogen peroxide flowing therethrough. Catalytic destroyer 94 converts hydrogen peroxide into water ($H_2O$) and oxygen ($O_2$). A second filter 114 and a heater 116 are disposed within return line 46 between blower 82 and vaporizer 32. Second filter 114 is operable to filter the air circulating through return conduit 46. Heater 116 is operable to heat air blown through return conduit 46 by blower 82. In this respect, air is heated prior to entering vaporizer 32. The heated air facilitates vaporization in vaporizer 32.

It should be understood that while an illustrated embodiment of the present invention is described in connection with a decontamination system 10 that does not include a drying apparatus (e.g., a desiccant dryer), it is contemplated that an optional dryer 85 may be disposed within return line 46 to remove moisture from air circulating through the circulation system. Optional dryer 85 may be used for situations where the air within region 22 has such a high level of humidity that a sufficient concentration of vaporized decontaminant (i.e., a concentration sufficient to effect decontamination of the region) cannot be held in the air.

A humidity sensor 122, a temperature sensor 124, and a hydrogen peroxide concentration sensor 128 are disposed within region 24. Humidity sensor 122 is operable to sense the relative humidity (RH) within region 24. Temperature probe 124 is operable to sense temperature within region 24. Absolute humidity may be determined from the RH and temperature sensed respectively by humidity sensor 122 and temperature sensor 124, or alternatively humidity sensor 122 can take the form of a sensor that directly measures absolute humidity. Hydrogen peroxide concentration sensor 128, e.g., an infrared sensor or an electrochemical sensor, is operable to sense the concentration of hydrogen peroxide within region 24. Humidity sensor 122 and temperature sensor 124 may be alternatively disposed within return line 46.

Humidity sensor 122, temperature sensor 124 and hydrogen peroxide concentration sensor 128 provide electrical signals to a system controller 132 that is schematically illustrated in FIG. 3. Controller 132 includes a microprocessor or microcontroller programmed to control the operation of decontamination system 10. Controller 132 also includes a memory or other data storage device. As illustrated in FIG. 3, controller 132 is also connected to motors 64, 84, and decontaminant supply 52. Controller 132 may also include input means (e.g., a keypad or buttons) and output means (e.g., a display, a speaker and/or a printer).

Controller 132 is programmed with a dew point margin ($\Delta_{MARGIN}$). The dew point margin ($\Delta_{MARGIN}$) is a delta value that is indicative of the minimum acceptable difference between: (1) the actual $H_2O_2$ concentration within region 24 and (2) the dew point concentration for the hydrogen peroxide vapor ($C_{DP}$), as calculated by controller 132. The dew point margin ($\Delta_{MARGIN}$) is used to prevent system 10 from operating in a manner wherein the actual $H_2O_2$ concentration ($C_{ACTUAL}$) exceeds the dew point concentration for the hydrogen peroxide vapor ($C_{DP}$). As a result, condensation of hydrogen peroxide inside region 24 is prevented.

During the conditioning and decontamination phases of the decontamination cycle, controller 132 controls system 10 to prevent condensation of hydrogen peroxide within region 24 by insuring that the actual hydrogen peroxide concentration ($C_{ACTUAL}$) within region 24 does not exceed the $H_2O_2$ dew point concentration ($C_{DP}$) within region 24. In this regard, controller 132 uses data provided by humidity sensor 122 together with data provided by temperature sensor 124, to calculate the absolute humidity within region 24. As indicated above, humidity sensor 122 may alternatively take the form of a sensor that directly measures absolute humidity. Using the absolute humidity, controller 132 determines the dew point concentration for the hydrogen peroxide vapor ($C_{DP}$), at the temperature within region 24. Controller 132 also monitors the actual $H_2O_2$ concentration ($C_{ACTUAL}$) within region 24 using $H_2O_2$ concentration sensor 128.

Controller 132 determines a measured delta value ($\Delta_{MEASURED}$) that is the difference between: (1) the actual $H_2O_2$ concentration ($C_{ACTUAL}$) inside region 24 and (2) the dew point concentration for the hydrogen peroxide vapor ($C_{DP}$). If the measured delta value ($\Delta_{MEASURED}$) is less than or equal to the dew point margin ($\Delta_{MARGIN}$), then the actual $H_2O_2$ concentration ($C_{ACTUAL}$) is approaching too close to the dew point concentration for the hydrogen peroxide vapor ($C_{DP}$). Accordingly, controller 132 takes appropriate action to increase the measured delta value ($\Delta_{MEASURED}$) to a value greater than the dew point margin ($\Delta_{MARGIN}$). In the illustrated embodiment, controller 132 increases the measured delta value ($\Delta_{MEASURED}$) to a value greater than the dew point margin ($\Delta_{MARGIN}$) by decreasing the injection rate of the aqueous solution of hydrogen peroxide to vaporizer 32, thereby reducing the actual $H_2O_2$ concentration ($C_{ACTUAL}$) within region 24. Controller 132 may also modify operation of blower 82 in order to decrease the air flow rate. The injection rate and/or air flow rate may be reduced to zero.

Figure 4:
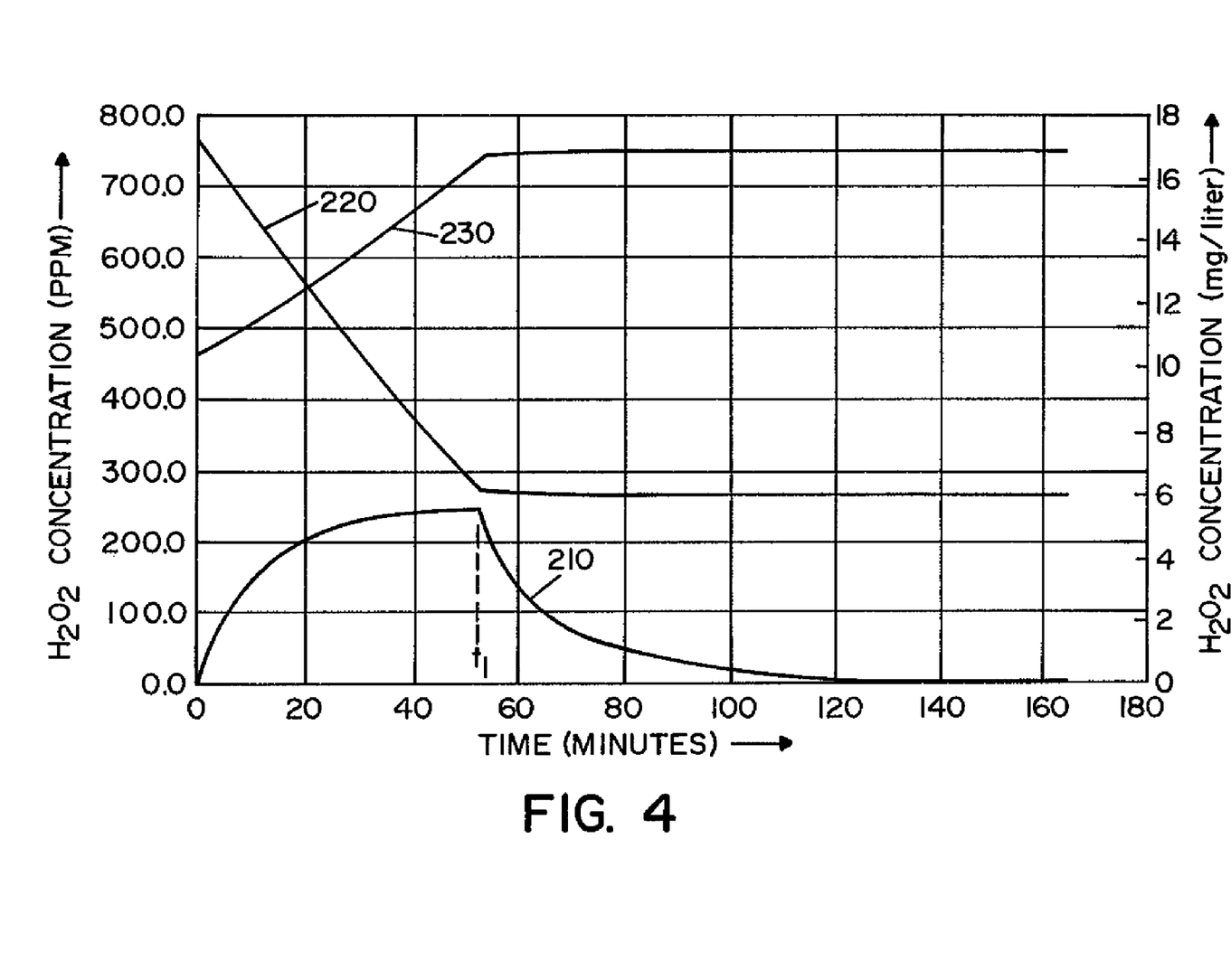
FIG. 4 shows a graph of hydrogen peroxide concentration, water concentration and $H_2O_2$ dew point concentration as a function of time, during conditioning and decontamination phases of a vaporized hydrogen peroxide decontamination procedure according to the present invention.

FIG. 4 illustrates a situation where there is no airflow or decontaminant injection after time $t_1$. The decrease in hydrogen peroxide concentration occurs due to the decay of the hydrogen peroxide as a result of half-life and catalytic affects.

As shown in FIG. 4, at time ti, the actual concentration of hydrogen peroxide ($C_{ACTUAL}$) within region 24 decreases due to decay of the hydrogen peroxide. As a result, $C_{ACTUAL}$ (shown as reference line 210) does not exceed $C_{DP}$ (shown as reference line 220). It is also observed in FIG. 4 that the water concentration (shown as reference line 230) increases as $C_{ACTUAL}$ (210) increases.

Figure 5:
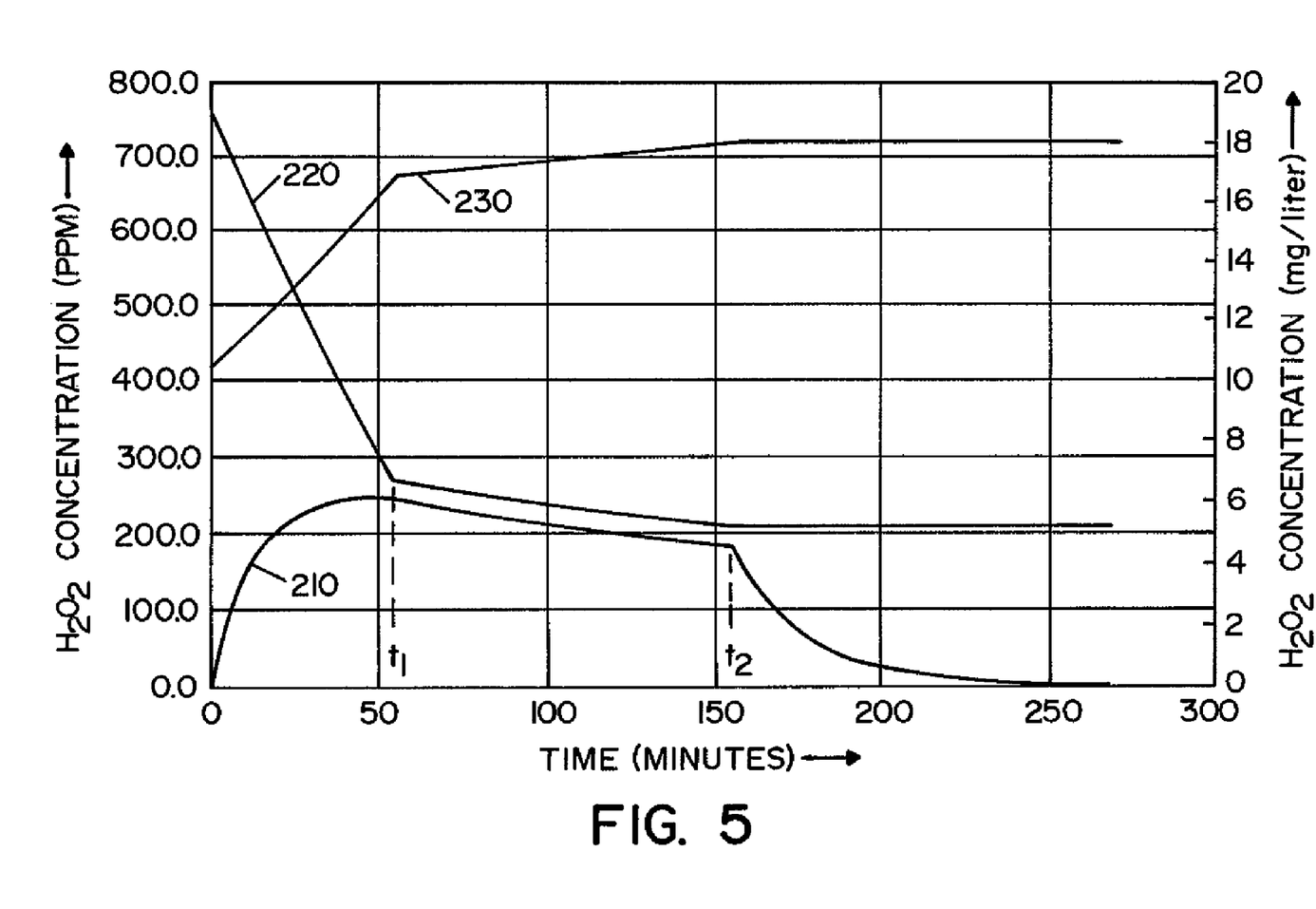
FIG. 5 shows another graph of hydrogen peroxide concentration, water concentration and $H_2O_2$ dew point concentration as a function of time, during conditioning and decontamination phases of a vaporized hydrogen peroxide decontamination procedure according to the present invention.

According to the control scheme illustrated by FIG. 5, injection of the aqueous solution of hydrogen peroxide to vaporizer 32 and the air flow produced by blower 82 may be "pulsed" on and off during the decontamination phase in order to prevent condensation of the hydrogen peroxide within region 24. In the graph shown in FIG. 5, at time $t_1$ through time $t_2$, controller 132 regulates the injection rate of the aqueous solution of hydrogen peroxide and the air flow rate, in order to maintain a substantially constant measured delta value ($\Delta_{MEASURED}$) between $C_{DP}$ and $C_{ACTUAL}$ that is greater than the dew point margin ($\Delta_{MARGIN}$). The actual concentration of hydrogen peroxide ($C_{ACTUAL}$) within region 24 (see line 210) does not remain at a constant value throughout the decontamination phase. However, in the control scheme illustrated by FIG. 5, the actual hydrogen peroxide concentration (line 210) is maintained at a maximum level, while also preventing condensation by maintaining the measured delta value ($\Delta_{MEASURED}$) at a level that is greater than the dew point margin ($\Delta_{MARGIN}$).

In accordance with the present invention, controller 132 calculates the bioburden reduction throughout the decontamination phase in order to determine whether a desired bioburden reduction has been achieved, thereby completing the decontamination phase. In this regard, the present invention provides a method for estimating bioburden reduction throughout a decontamination phase, even when the $H_2O_2$ concentration varies throughout the decontamination phase. It has been recognized that an estimate of bioburden reduction can be obtained by integrating an $H_2O_2$ concentration vs. time curve.

A D-value is used to express the length of time (i.e., "decimal reduction time") required for a one log reduction of bioburden (i.e., a 90% reduction in the viable microbial population). Accordingly, xD expresses the time (usually in minutes) required for x log reduction of bioburden. A typical biological indicator (BI) for a vaporized hydrogen peroxide decontamination system is populated with $10^6$ spores, such as *Geobacillus stearothermophilus*. Thus, to obtain a "kill" of 6 log reduction of the *Geobacillus stearothermophilus* spores, the article being decontaminated must be exposed to vaporized hydrogen peroxide at a predetermined concentration for a corresponding exposure time.

The U.S. Environmental Protection Agency (EPA) has established standards for vaporized hydrogen peroxide decontamination systems that require a hydrogen peroxide concentration of 250 ppm for 90 minutes or a hydrogen peroxide concentration of 400 ppm for 30 minutes. However, in accordance with the present invention, the hydrogen peroxide concentration within region 24 may not remain substantially constant at a predetermined concentration, since it may be necessary to vary the hydrogen peroxide concentration within region 24 in order to prevent condensation of the hydrogen peroxide.

Figure 6:
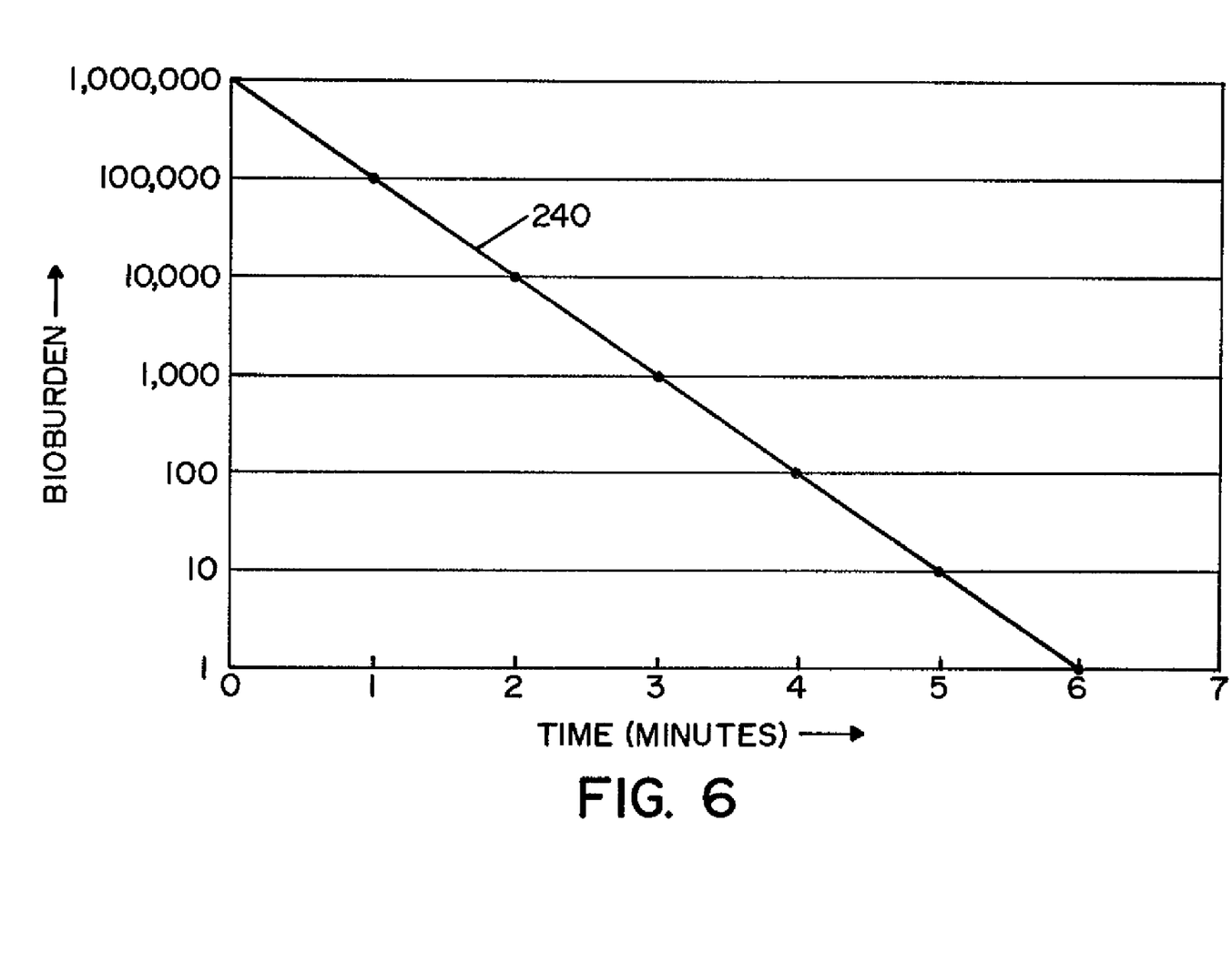
FIG. 6 shows a graph of bioburden (i.e., spore population) as a function of time during a decontamination procedure, where the D-value equals 1 minute.

Assuming that the D-value for a given concentration of vaporized hydrogen peroxide is a constant 1 minute, regardless of the population of bioburden (i.e., spores), then the relationship of "bioburden vs. time" shown in FIG. 6 is representative. Reference line 240 shows that the bioburden is reduced by 90% every 1 minute. Accordingly, the reduction of bioburden is log-linear in accordance with the foregoing assumption.

Figure 7:
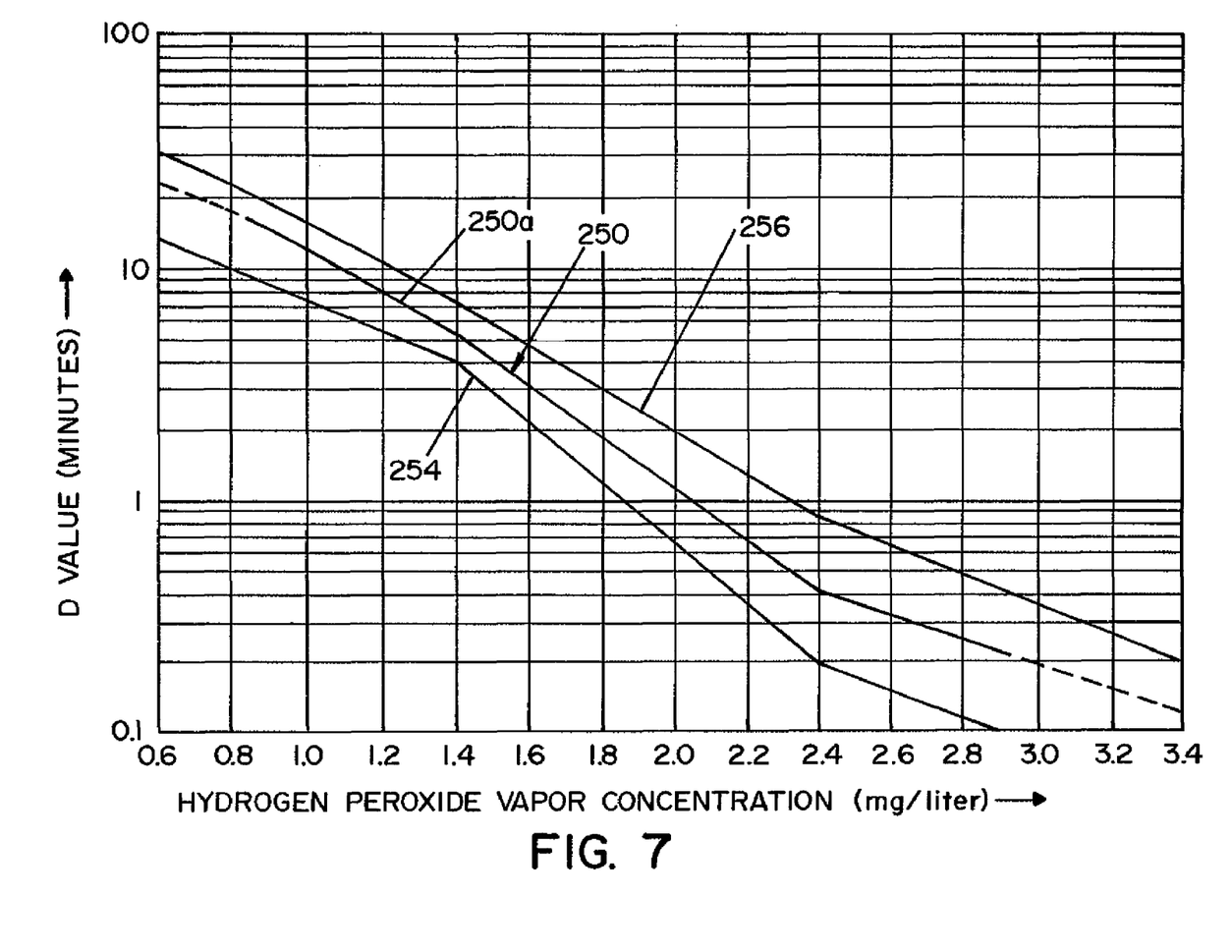
FIG. 7 shows a graph of D-values (minutes) in a logarithmic scale as a function of hydrogen peroxide vapor concentration (mg/liter)

To account for a changing or transient hydrogen peroxide concentration within region 24, the D-value must be established for a given time. Previously determined D-value vs. hydrogen peroxide concentration curves have shown that the D-value vs. hydrogen peroxide concentration is also log-linear for given regions. FIG. 7 shows D-value (minutes) as a function of vaporized hydrogen peroxide concentration. Reference line 250 represents the "Best Fit," reference line 254 represents the "One Sigma Low" and reference line 256 represents the "One Sigma High." Section 250a is the region of the "Best Fit" having a log-linear relationship. For such log-linear regions, the relationship between D-value and vaporized hydrogen peroxide concentration can be expressed as:

$$\text{Log}(D) = (m \cdot C + b)(S) \qquad (1)$$

Where:
D=D-value=time (minutes) required for a 1 log reduction in bioburden,
m=slope from the D-value vs. vaporized hydrogen peroxide curve,
C=concentration of vaporized hydrogen peroxide (mg/l or ppm),
b=y-intercept from D-value vs. vaporized hydrogen peroxide curve,
S=a fractional value between 1.0 and 0 that is associated with the effect of saturation level. In some cases, the D-value is dependant on the saturation level of the decontaminant (100% saturation is achieved at the dew point concentration of the decontaminant). The S value is described in further detail in the STERIS® VHP Cycle Development Guide, incorporated herein by reference.

In accordance with a log-linear relationship for D-value vs. vaporized hydrogen peroxide concentration, the value for m and b can be found using two known hydrogen peroxide concentrations and associated D-values. Solving for D gives:

$$D = 10^{[(m \cdot C + b)(S)]} \qquad (2)$$

Equation (2) can be used to determine the D-value for any hydrogen peroxide concentration within a linear region bounded by two hydrogen peroxide concentrations, with known associated D-values (e.g., see section 250a of reference line 250).

Figure 8:
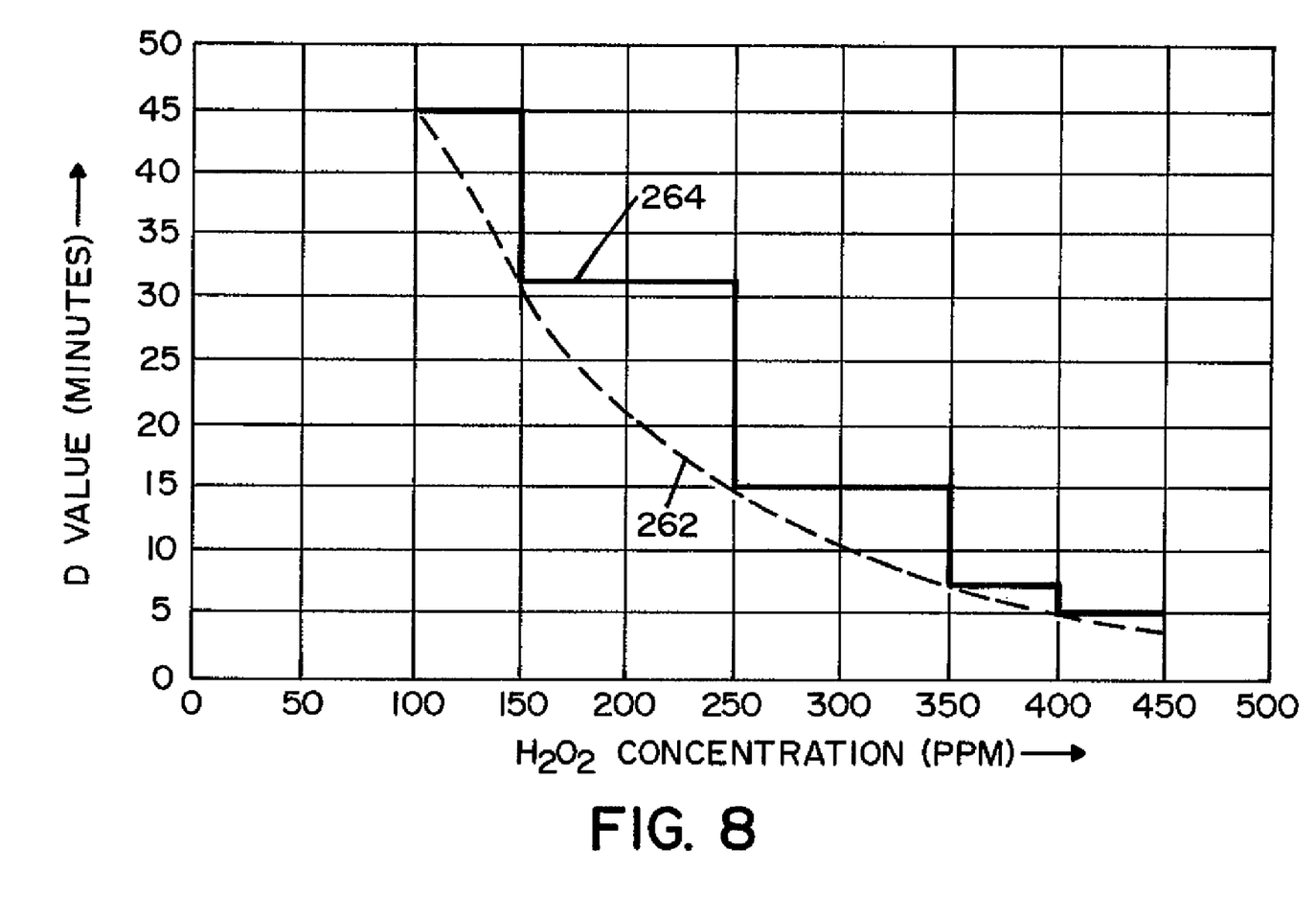
FIG. 8 shows a graph of D-values (minutes) in stepped increments as a function of hydrogen peroxide vapor concentration (mg/liter).

It should be understood that D-values as a function of hydrogen peroxide concentration can also be expressed as a "step graph." In this respect, a single D-value is associated with a range of hydrogen peroxide concentrations. For example, in FIG. 8, a D-value of 45 minutes is associated with a hydrogen peroxide concentration range of 100 ppm to 150 ppm. The appropriate D-value for a range of hydrogen peroxide concentrations is determined through testing. For example, a D-value is determined for various hydrogen peroxide concentrations (e.g., 100 ppm, 150 ppm, 200 ppm, 250 ppm, 300 ppm, 350 ppm and 400 ppm). A D-value that is greater than or equal to the actual D-value is associated with a range of hydrogen peroxide concentrations. In FIG. 8, actual D-values are shown as line 262, while the "step" D-values are shown as line 264.

In accordance with the graph shown in FIG. 6, bioburden as a function of time can be expressed as follows:

$$\text{Log}(B) = m \cdot dt + b \quad (3)$$

where:
B=the bioburden (i.e., the number of spores),
m=slope of the log(B) vs. time curve (i.e., rate of bioburden reduction),
dt=time step or increment (minutes), and
b=the y-intercept of the log(B) vs. time curve=initial bioburden (i.e., the initial number of spores).

Since the slope m (i.e., rate of bioburden reduction) in FIG. 6 is equal to −1/D, then $$B = 10^{(\frac{-1}{D} dt + b)} \quad (4)$$

Equation (4) provides the value of the bioburden B as a function of the D-value and the initial bioburden (b). Accordingly, the remaining bioburden B may be determined for a given time step.

It should be understood that the control strategy embodied in the present invention requires that the water and hydrogen peroxide concentrations within region 24 are known.

Operation of system 10 will now be described in detail. Initial data are stored in controller 132. The initial data include, but are not limited to, the volume of region 24 ($V_{REGION}$); a kill threshold concentration; data indicative of D-values as a function of hydrogen peroxide concentration; a time step (dt); a dew point margin ($\Delta_{MARGIN}$); a maximum allowable humidity level; an initial bioburden (b) and a target bioburden reduction ($\Delta B_{TARGET}$).

The kill threshold concentration is a minimum hydrogen peroxide concentration that must be present within region 24 before bioburden B is determined. In this regard, bioburden B is assumed to remain at its original level until the kill threshold concentration has been reached. In the illustrated embodiment of the present invention, any bioburden reduction resulting from hydrogen peroxide concentrations below the kill threshold concentration is not considered when determining whether a target bioburden reduction $\Delta B_{TARGET}$ has been achieved. 100551 Data indicative of D-values as a function of hydrogen peroxide concentration may be stored in controller 132 in the form of data representative of the curve shown in FIG. 7, data representative of the step graph shown in FIG. 8, or as equation (2).

The time step (dt) is the time increment for determining bioburden B using equation (4).

As discussed above, the dew point margin ($\Delta_{MARGIN}$) is a delta value that is indicative of the minimum acceptable difference between: (1) the actual $H_2O_2$ concentration within region 24 and (2) the dew point concentration for the hydrogen peroxide vapor ($C_{DP}$), as calculated by controller 132.

The maximum allowable humidity level is the maximum level of water vapor that can be present in region 24 before vaporized hydrogen peroxide is injected into region 24. If the humidity level is too high, the air within region 24 will not hold a sufficient concentration of vaporized hydrogen peroxide to effect decontamination. In other words, the vaporized hydrogen peroxide will condense before reaching a suitable concentration within region 24. Therefore, in accordance with the present invention, vaporized hydrogen peroxide is not injected into region 24 unless the humidity level within region 24 is at or below the maximum allowable humidity level. The humidity level in region 24 may be determined using humidity sensor 122 and temperature sensor 124. If the humidity level remains above the maximum humidity level, it will be necessary to take some action to reduce the humidity within region 24. For example, optional dryer 85 may be added to system 10 in order to reduce the humidity level.

The initial bioburden (b) is the level of bioburden on a biological indicator (BI) located within region 24 at the commencement of a vaporized hydrogen peroxide treatment cycle. The target bioburden reduction ($\Delta B_{TARGET}$) is the amount by which the bioburden on the BI located within region 24 is to be reduced in order to achieve a successful decontamination.

As discussed above in connection with FIG. 1, a typical vaporized hydrogen peroxide treatment cycle of a vaporized hydrogen peroxide decontaminating system includes a drying phase, a conditioning phase, a decontamination phase and an aeration phase. In accordance with the illustrated embodiment of the present invention, the drying phase is eliminated, and the treatment cycle begins with the conditioning phase. Accordingly, if controller 132 determines that the humidity within region 24 is below the maximum allowable humidity level, then the conditioning phase is commenced, followed by the decontamination phase.

Upon commencement of the conditioning phase, vaporized hydrogen peroxide is rapidly increased in region 24. In this regard, controller 132 activates motor 64, thereby causing pump 62 to supply metered amounts of the aqueous solution of hydrogen peroxide (e.g., 30% to 59% hydrogen peroxide, by weight) to vaporizer 32. Vaporizer 32 produces vaporized hydrogen peroxide in a conventionally known manner. Controller 132 also activates motor 84, thereby causing blower 82 to supply vaporized hydrogen peroxide to region 24. The conditioning phase continues until the kill threshold is exceeded.

The decontamination phase follows the conditioning phase. As vaporized hydrogen peroxide is supplied to region 24, controller 132 determines the water concentration, temperature and hydrogen peroxide concentration levels within region 24 using sensors 122, 124 and 128. Once the hydrogen peroxide concentration within region 24 meets or exceeds the kill threshold concentration, controller 132 begins monitoring the bioburden within region 24. In this regard, bioburden B is repeatedly determined throughout the decontamination phase for each time step (dt), until the target bioburden reduction ($\Delta B_{TARGET}$) is achieved ("cycle success") or the concentration of hydrogen peroxide within region 24 drops below the kill threshold concentration ("cycle aborted").

For each time step (dt), controller 132 determines the D-value of the vaporized hydrogen peroxide within region 24 and calculates the bioburden (B) according to equation (4) above. The D-value is determined from the data indicative of D-values as a function of hydrogen peroxide concentration (e.g., the data of FIG. 7 or 8, or equation (2)). For the first time step (dt), the initial bioburden (b) is prestored, or entered by an operator. For each subsequent time step (dt), the bioburden B calculated for the preceding time step is used as the initial bioburden (b) in equation (4). Accordingly, the initial bioburden (b) may vary for each time step (dt), as the vaporized hydrogen peroxide effects decontamination within region 24.

As the bioburden B is determined for each respective time step (dt), the total bioburden reduction ($\Delta B_{TOTAL}$) is determined, and compared with the target bioburden reduction ($\Delta B_{TARGET}$). In this regard, controller 132 determines the bioburden reduction for a single time step ($\Delta B_{STEP}$) by calculating the difference between the initial bioburden (b) for that single time step (dt) and the calculated bioburden B for that single time step (dt). Thus, the total bioburden reduction ($\Delta B_{TOTAL}$) for a decontamination phase is the sum of all of the bioburden reductions for each time step ($\Delta B_{STEP}$) of the decontamination phase. Therefore, $$\Delta B_{TOTAL} = \Delta B_{STEPx} + \Delta B_{STEP(x-1)} + \Delta B_{STEP(x-2)} \cdots + \Delta B_{STEP(1)},$$

where x is the total number of completed time steps (dt) of the decontamination phase.

Controller 132 compares the total bioburden reduction ($\Delta B_{TOTAL}$) to the target bioburden reduction ($\Delta B_{TARGET}$). If the target bioburden reduction ($B_{TARGET}$) has been achieved, then the decontamination phase has been successfully completed, and controller 132 commences the aeration phase. If the target bioburden reduction ($B_{TARGET}$) has not been achieved, then the decontamination phase continues for one or more additional time steps. Controller 132 determines the total bioburden reduction ($\Delta B_{TOTAL}$) after the completion of each time step in order to continuously monitor the bioburden reduction within region 24.

Throughout the conditioning and decontamination phases, controller 132 uses the measured absolute humidity and measured hydrogen peroxide concentration within region 24 to determine in a conventionally known manner the dew point concentration for the hydrogen peroxide vapor ($C_{DP}$), at the temperature inside region 24.

During the conditioning and decontamination phases, controller 132 also continuously monitors the dew point concentration and the measured delta value ($\Delta_{MEASURED}$) in order to maintain the measured delta value ($\Delta_{MEASURED}$) at a value greater than the dew point margin ($\Delta_{MARGIN}$). A detailed description of the operation of controller 132 is found in U.S. patent application Ser. No. 11/741,069, filed Apr. 27, 2007, entitled "VAPORIZED HYDROGEN PEROXIDE DECONTAMINATION SYSTEM WITH CONCENTRATION ADJUSTMENT MODE," and hereby fully incorporated herein by reference.

If $\Delta_{MEASURED}$ (i.e., difference between: the actual $H_2O_2$ concentration ($C_{ACTUAL}$) inside region 24 and the dew point concentration for the hydrogen peroxide vapor ($C_{DP}$)) is less than or equal to the dew point margin ($\Delta_{MARGIN}$), then the amount of vaporized hydrogen peroxide supplied to region 24 is decreased. For example, the injection of the aqueous solution of hydrogen peroxide to vaporizer 32 may be reduced or suspended, and/or the air flow produced by blower 82 may be reduced or suspended. During this time, the hydrogen peroxide concentration level will decrease as a result of various factors, such as half-life and adsorption. The supply of vaporized hydrogen peroxide to region 24 is increased once $\Delta_{MEASURED}$ is greater than $\Delta_{MARGIN}$. It should be understood that the amount of vaporized hydrogen peroxide supplied to region 24 may vary throughout the decontamination phase as $\Delta_{MEASURED}$ changes.

The present invention provides a method and apparatus by which a region may be decontaminated without the need for dehumidification to prevent condensation of vaporized hydrogen peroxide. The control scheme includes continuous monitoring of the bioburden reduction within the region, thereby allowing successful completion of a decontamination phase to be readily ascertained.

As described in detail above, the dew point concentration of the decontaminant (e.g., hydrogen peroxide) varies in response to the humidity level within the region. However, it will be appreciated that other parameters within the region also influence the dew point concentration of the decontaminant, including, but not limited to, temperature within the region. Accordingly, it is contemplated that controller 132 may be programmed to regulate the concentration of the gaseous or vaporous decontaminant (e.g., hydrogen peroxide) within a region in response to one or more parameters influencing the dew point concentration of the decontaminant, without condensation of the gaseous or vaporous decontaminant. For example, when the temperature in the region increases, due to heating of the region, it may be possible to increase the concentration of the gaseous or vaporous decontaminant within the region without condensation of the decontaminant.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, in the illustrated embodiment of the present invention, the liquid decontaminant is an aqueous solution of hydrogen peroxide. It is contemplated that the present invention may find advantageous application with decontamination systems using other gas or vapor-phase decontaminants. In such alternative embodiments, the saturation concentration of interest will be the saturation concentration of the other vapor-phase decontaminants. It is also contemplated that the present invention may find advantageous application in decontamination systems that include the use of a drying apparatus. It is intended that all such modifications and alterations be included insofar as they come within the scope of the invention as claimed or the equivalents thereof.

Having described the invention, the following is claimed:

1. A method for decontaminating a region with a vaporized decontaminant, the method comprising the steps of:
   supplying vaporized decontaminant into the region for obtaining at least a minimum concentration level of the vaporized decontaminant in the region;
   monitoring the concentration of the vaporized decontaminant in the region;
   determining the dew point concentration of the vaporized decontaminant in the region;
   regulating the supply of vaporized decontaminant into the region to maintain the concentration of vaporized decontaminant to at least a predetermined amount below the dew point concentration of the vaporized decontaminant;
   determining a bioburden reduction for each of one or more time increments of a decontamination process, wherein determining said bioburden reduction for each time increment includes:
   establishing an initial bioburden within the region;
   determining a D-value associated with the concentration of vaporized decontaminant within the region, wherein said D-value is a time required for a 1 log reduction in bioburden; and
   calculating a bioburden within the region in accordance with the initial bioburden, the time increment and the D-value;
   calculating a total bioburden reduction within the region by summing said bioburden reduction determined for each of said one or more time increments;
   determining whether a decontamination process is complete by comparing the total bioburden reduction within the region to a target bioburden reduction; and
   continuing the decontamination process for at least one additional time increment until the total bioburden reduction within the region has achieved the target bioburden reduction.

2. A method according to claim 1, wherein determining said bioburden reduction for each time increment further comprises:
    comparing the initial bioburden with the calculated bioburden.

3. A method according to claim 1, wherein said vaporized decontaminant is vaporized hydrogen peroxide.

4. A vapor decontamination system for decontaminating a region, said system comprising:
    a decontaminant supply for providing a supply of liquid decontaminant;
    a vaporizer for generating a vaporized decontaminant, said vaporizer receiving liquid decontaminant from the decontaminant supply;
    a circulating system for supplying said vaporized decontaminant to said region; and
    control means programmed to:
        monitor the concentration of the vaporized decontaminant in the region;
        determine the dew point concentration of the vaporized decontaminant in the region;
        regulate the supply of vaporized decontaminant into the region to maintain the concentration of vaporized decontaminant at least a predetermined amount below the dew point concentration of the vaporized decontaminant;
        determine a bioburden reduction for each of one or more time increments of a decontamination process, wherein said control means is programmed to determine said bioburden reduction for each time increment by:
            establishing an initial bioburden within the region;
            determining a D-value associated with the concentration of vaporized decontaminant within the region, wherein said D-value is a time required for a 1 log reduction in bioburden; and
            calculating a bioburden within the region in accordance with the initial bioburden, the time increment and the D-value;
        calculate a total bioburden reduction within the region by summing said bioburden reduction for each of said one or more time increments; and
        determine whether a decontamination process is complete by comparing the total bioburden reduction within the region to a target bioburden reduction, wherein the decontamination process is continued for at least one additional time increment until the total bioburden reduction within the region has achieved the target bioburden reduction.

5. A vapor decontamination system according to claim 4, wherein said system further comprises:
    at least one humidity sensor providing a first signal indicative of moisture in the region;
    a temperature sensor providing a second signal indicative of the temperature in the region; and
    at least one concentration sensor providing a third signal indicative of the concentration of the decontaminant in the region.

6. A vapor decontamination system according to claim 4, wherein said control means is programmed to determine said bioburden reduction for each time increment by:
    comparing the initial bioburden with the calculated bioburden.

7. A vapor decontamination system according to claim 4, wherein said vaporized decontaminant is vaporized hydrogen peroxide.

8. A method for decontaminating a region with vaporized hydrogen peroxide, the method comprising the steps of:
    supplying vaporized hydrogen peroxide into the region;
    monitoring the concentration of the vaporized hydrogen peroxide in the region;
    regulating the supply of vaporized hydrogen peroxide into the region to maintain the concentration of vaporized hydrogen peroxide below the dew point concentration of the vaporized hydrogen peroxide;
    determining a bioburden reduction for each of one or more time increments of a decontamination process, wherein determining said bioburden reduction for each of said one or more time increments includes:
        establishing an initial bioburden within the region;
        determining a D-value associated with the concentration of vaporized decontaminant within the region, wherein said D-value is a time required for a 1 log reduction in bioburden; and
        calculating a bioburden within the region in accordance with the initial bioburden, the time period and the D-value;
    repeatedly calculating a total bioburden reduction within the region during the decontamination process in accordance with the bioburden reduction determined for each of said plurality of time increments, said total bioburden reduction calculated at the completion of each time increment of the decontamination process;
    determining whether the decontamination process is complete by comparing the calculated total bioburden reduction to a target bioburden reduction; and
    continuing the decontamination process until the calculated total bioburden reduction within the region has achieved the target bioburden reduction.

9. A method according to claim 8, wherein said total bioburden reduction within the region is calculated by summing said bioburden reduction for each of said one or more time increments of the decontamination process.

10. A method according to claim 8, wherein determining said bioburden reduction for each of said time increments further comprises:
    comparing the initial bioburden with the calculated bioburden.

11. A method for decontaminating a region with a vaporized decontaminant, the method comprising the steps of:
    supplying vaporized decontaminant into the region;
    monitoring at least one parameter influencing the dew point concentration of the vaporized decontaminant in the region;
    regulating the supply of vaporized decontaminant introduced into the region to maintain the concentration of vaporized decontaminant within the region at a level below the dew point concentration of the vaporized decontaminant;
    determining a bioburden reduction for each of one or more time increments of a decontamination process, wherein determining said bioburden reduction for each time increment includes:
        establishing an initial bioburden within the region;
        determining a D-value associated with the concentration of vaporized decontaminant within the region, wherein said D-value is a time required for a 1 log reduction in bioburden; and
        calculating a bioburden within the region in accordance with the initial bioburden, the time increment and the D-value;

calculating a total bioburden reduction within the region by summing said bioburden reduction determined for each of said one or more time increments; and continuing a decontamination process for at least one additional time increment until the total bioburden reduction within the region has at least achieved a target bioburden reduction.

12. A method according to claim 11, wherein said at least one parameter includes humidity level within said region.

13. A method according to claim 11, wherein said at least one parameter includes temperature within said region.

14. A method according to claim 11, wherein said step of calculating the total bioburden reduction within the region includes determining a bioburden reduction for one or more time increments.

15. A method according to claim 14, wherein said bioburden reduction for each of said time increments is summed to obtain the total bioburden reduction within the region.

16. A method according to claim 11, wherein determining said bioburden reduction for each time increment further comprises:

comparing the initial bioburden with the calculated bioburden.

17. A method according to claim 11, wherein said vaporized decontaminant is vaporized hydrogen peroxide.

18. A vapor decontamination system for decontaminating a region, said system comprising:

a vaporizer for generating a vaporized decontaminant, said generator receiving liquid decontaminant from the decontaminant supply;

a circulating system for supplying said vaporized decontaminant to said region; and control means programmed to:

monitor at least one parameter influencing the dew point concentration of the vaporized decontaminant in the region;

regulate the supply of vaporized decontaminant introduced into the region to maintain the concentration of vaporized decontaminant within the region at a level below the dew point concentration of the vaporized decontaminant;

determine a bioburden reduction for each of one or more time increments of a decontamination process, wherein said bioburden reduction for each time increment is determined according to a D-value and initial bioburden within the region, said D-value determined as a function of concentration of the vaporized decontaminant within the region, wherein said D-value is a time required for a 1 log reduction in bioburden;

calculate a total bioburden reduction within the region by summing said bioburden reduction determined for each of said one or more time increments; and continue a decontamination process for at least one additional time increment until the total bioburden reduction within the region has at least achieved a target bioburden reduction.

19. A vapor decontamination system according to claim 18, wherein said at least one parameter includes humidity level within said region.

20. A vapor decontamination system according to claim 18, wherein said at least one parameter includes temperature within said region.

* * * * *